United States Patent [19]
Rabin et al.

[11] Patent Number: 5,894,842
[45] Date of Patent: Apr. 20, 1999

[54] PESSARY FOR TREATING VAGINAL PROLAPSE

[75] Inventors: Jill M. Rabin; Ashlesha Dayal, both of New York, N.Y.

[73] Assignee: Long Island Jewish Medical Center, New Hyde Park, N.Y.

[21] Appl. No.: 09/132,415

[22] Filed: Aug. 11, 1998

[51] Int. Cl.[6] .................................................. A61F 6/06
[52] U.S. Cl. .................................. 128/830; 128/834
[58] Field of Search ........................ 128/830–841

[56] References Cited

U.S. PATENT DOCUMENTS

| | | | |
|---|---|---|---|
| 40,949 | 12/1863 | Scattergood | 128/834 |
| 178,458 | 6/1876 | Otto | 128/834 |
| 328,553 | 10/1885 | Wamoth | 128/834 |
| 804,086 | 11/1905 | Barchfeld | 128/834 |
| 1,926,518 | 9/1933 | Findley . | |
| 2,574,767 | 11/1951 | Stubbs . | |
| 2,613,670 | 10/1952 | Sokolik | 128/834 |
| 3,967,618 | 7/1976 | Zaffaroni . | |
| 4,307,716 | 12/1981 | Davis . | |
| 4,516,570 | 5/1985 | Taban . | |
| 4,677,967 | 7/1987 | Zartman . | |
| 4,724,832 | 2/1988 | Strubel et al. . | |
| 4,823,814 | 4/1989 | Drogendijk et al. . | |
| 5,224,494 | 7/1993 | Enhorning . | |
| 5,355,896 | 10/1994 | Schulman . | |
| 5,771,900 | 6/1998 | Austin | 128/834 |

FOREIGN PATENT DOCUMENTS 501023  6/1930  Germany .

*Primary Examiner*—Michael A. Brown
*Attorney, Agent, or Firm*—Amster, Rothstein & Ebenstein

[57] ABSTRACT

An intravaginal pessary for treating prolapses includes a flexible core having a longitudinal axis and being disposed in a three dimensional configuration. The longitudinal dimension of the core along its longitudinal axis is modifiable within limits by manual pressure, both before and after insertion of the pessary into a vagina, the core being non-resiliently expandable and contractible within limits to modify the longitudinal dimension. A first longitudinal portion of the core is meshingly engageable with a second longitudinal portion of the core intersecting the first longitudinal portion of the core to lock within limits the longitudinal dimensions of the core intermediate the first and second longitudinal portions. The first and second longitudinal portions are manually separable, both before and after insertion of the pessary into the vagina, to unlock the longitudinal dimension of the core intermediate the first and second longitudinal portions. A thin flexible casing of biocompatible and deformable gel encloses the core without precluding such locking and unlocking thereof.

9 Claims, 3 Drawing Sheets

PESSARY FOR TREATING VAGINAL PROLAPSE

BACKGROUND OF THE INVENTION

The present invention relates to a pessary for treating prolapse of a vagina, and more particularly to such a pessary having a variable longitudinal dimension.

Intravaginal pessaries are support devices intended to reduce pelvic organ prolapse (e.g., cervical, uterine, vaginal, bladder and/or rectal prolapse). They are varied in type and size and are typically fitted according to the individual patient's anatomy. One of the problems encountered by the majority of pessary users over time is the development of intravaginal ulcers due to pressure necrosis.

An optimum vaginal support device should supplant torn or broken endopelvic facia or weak vaginal muscle with maximum support in the area of the specific individualized pelvic floor defect (whether muscular weakness or facial tear) without undue pressure on the delicate vaginal mucosa. An optimum pessary must adapt to the fact that most introituses are smaller than the vaginal cavity which they are meant to occupy in order to support the pelvic floor defects, yet the pessary must be large enough to correct all pelvic floor defects and small enough and delicate enough to fit even the smallest introitus (i.e., vaginal opening) and cause the least amount of pelvic floor problems such as infection or ulceration. A three dimensional pessary is preferred in order that the pessary used for an individual pelvic type may be stretched after insertion to fill the area where the specific pelvic floor defects exist (such as inferiorly toward the lateral vaginal wall support, medially toward the cervix or upper vaginal vault, posteriorly to correct rectocele or laterally, to correct a lower lateral vaginal wall support defect). The object of the pessary is to restore the patient's original anatomy with a minimum of obstruction and pressure on the delicate surrounding tissues, and thereby requires an optimum fit to obtain maximum comfort.

U.S. Pat. No. 4,823,814 discloses a pessary particularly applicable in the treatment of prolapses of internal female sex organs such as the vagina. The pessary is formed by a ring-shaped member constructed of materials which can be deformed by hand to any given shape and the circumferential dimension of the ring can be increased or decreased to some extent by hand, after which the ring retains the ultimately given shape and circumferential dimension. Preferably the ring consists of a core which has the shape of a spiral of non-resilient nature and a flexible casing enclosing the core. While the patented pessary is today in common use, it has not proven to be entirely satisfactory.

Ideally, the pessary will have a three dimensional configuration so that it can be used for the treatment of several defects at once. One defect of the aforementioned pessary disclosed in U.S. Pat. No. 4,823,814 is that the ring structure is essentially planar, rather than three dimensional, and thus cannot be used to treat several prolapses at the same time. A further defect is that the exertion of pressure on the pessary—whether a manual pressure as used to insert it through the introitus into the vaginal cavity or the pressure exerted on the pessary by the vaginal walls after insertion (as opposed to during insertion)—may deform the pessary from its contemplated configuration so that it is no longer capable of performing its intended function.

Accordingly, it is an object of the present invention to provide an intravaginal pessary for treating prolapses wherein the longitudinal length of the pessary intermediate two portions thereof may be fixed within limits.

Another object is to provide such a pessary wherein the longitudinal dimension may be locked or fixed within limits.

A further object is to provide such a pessary wherein the longitudinal dimension may be unlocked or unfixed so as to enable modification thereof.

SUMMARY OF THE INVENTION

It has now been found that the above and related objects of the present invention are obtained in an intravaginal pessary for treating prolapses comprising a flexible core and a flexible casing. The flexible core has a longitudinal axis and is disposed in a twisted three-dimensional configuration. The longitudinal dimension of the core, along its longitudinal axis, is modifiable within limits by manual pressure both before and after insertion of the pessary into a vagina. The core is non-resiliently expandable and contractible within limits to modify the longitudinal dimension of the core. A first longitudinal portion of the core is meshingly engageable with a second longitudinal portion of the core intersecting the first longitudinal portion of the core to lock the longitudinal dimension of the core intermediate the first and second longitudinal portions. Further, the First and second longitudinal portions are manually separable both before and after insertion of the pessary into the vagina to unlock the longitudinal dimension of the core intermediate the first and second longitudinal portions. The casing is a flexible casing of bio-compatible and deformable material (preferably a gel) enclosing the core without precluding such locking and unlocking thereof.

In one preferred embodiment, at least one of the ridges along a first longitudinal portion of the core is meshingly engageable with at least an adjacent pair of the ridges along a second longitudinal portion of the core intersecting the first longitudinal portion of the core, thereby to lock the longitudinal dimension of the core intermediate the first or second longitudinal portions. The at least one ridge and the adjacent pair of ridges are manually separable both before and after insertion of the pessary into the vagina to unlock the longitudinal dimension of the core intermediate the first and second longitudinal portions.

In another preferred embodiment, at least an adjacent pair of the ridges along the first longitudinal portion of the core meshingly engage at least an adjacent pair of the ridges along a second longitudinal portion of the core intersecting the first longitudinal portion of the core. In a further preferred embodiment, only one of the ridges along the first longitudinal portion meshingly engages at least an adjacent pair of the ridges along the second longitudinal portion. The two adjacent pairs of ridges (or the one ridge and the adjacent pair of ridges) are manually engageable and separable.

Preferably the core is hollow.

The present invention further encompasses a method of treating prolapse of the vagina by use of a pessary. The method includes the steps of providing a pessary as described above, manually separating the at least one ridge and the adjacent pair of ridges, thereby to unlock the longitudinal dimension, expanding or contracting the grooves to modify the longitudinal dimension, and meshingly engaging at least the one ridge and the adjacent pair of ridges, thereby to lock the longitudinal dimension.

While locking of the circumferential dimension may be achieved by meshingly engaging only one of the ridges along the first longitudinal portion with at least an adjacent pair of the ridges along the second longitudinal portion, preferably at least an adjacent pair of the ridges along the first longitudinal portion are meshingly engaged with at least an adjacent pair of ridges along a second longitudinal portion of the core.

BRIEF DESCRIPTION OF THE DRAWING

The above and related objects, features and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
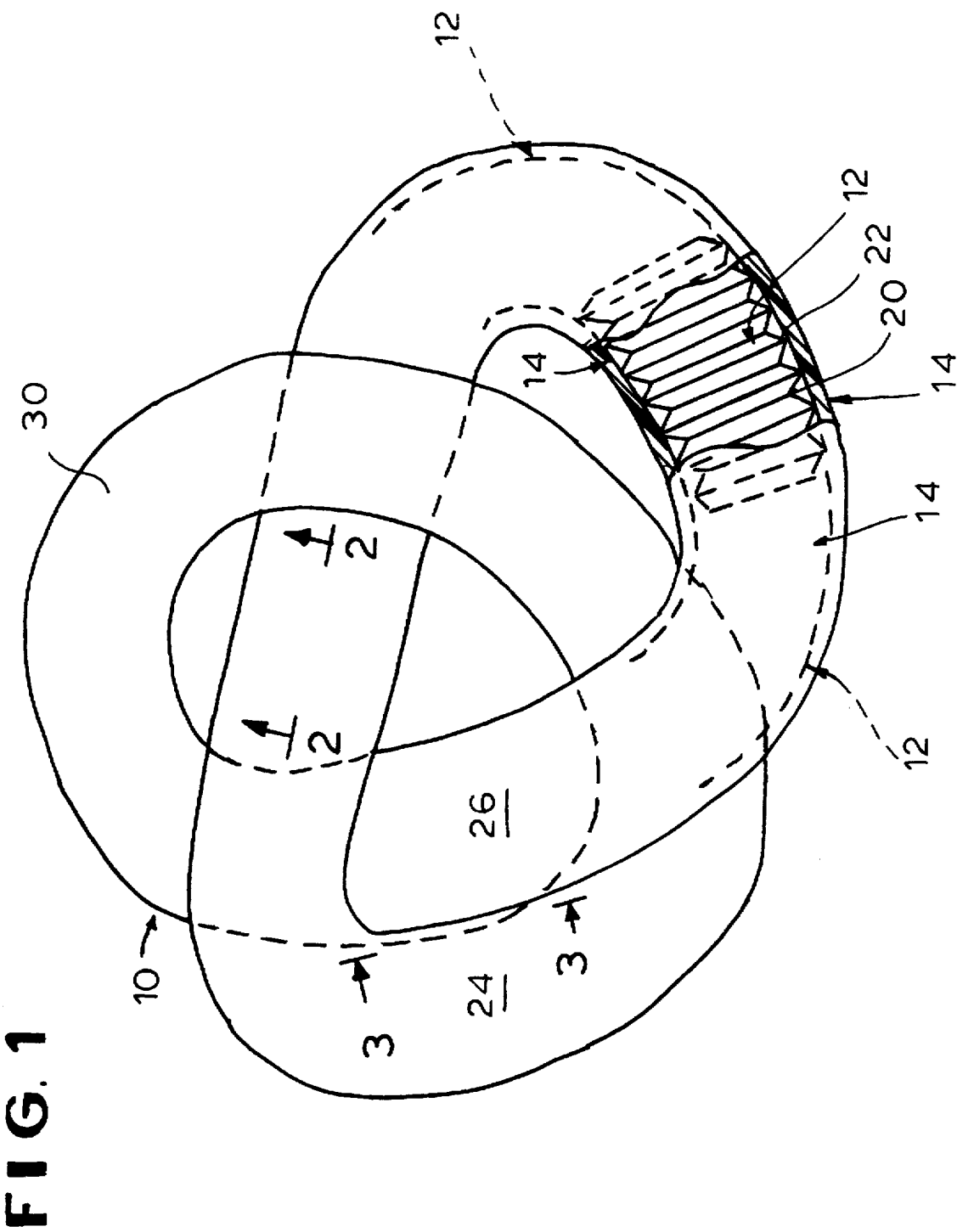
FIG. 1 is an isometric view of a pessary according to the present invention, with a segment of the casing removed to reveal details of internal core construction.

Referring now to the drawing, and in particular to FIG. 1 thereof, therein illustrated is an intravaginal pessary for treating prolapses of the female sex organs according to the present invention, generally designated by the reference numeral 10. The pessary 10 is comprised of a flexible core generally designated 12 and a flexible casing therefor generally designated 14.

More particularly, the flexible core 12 is preferably hollow and has a longitudinal axis (of a typically curvilinear configuration) extending within and along the hollow of the core. The core 12 is disposed in a twisted three dimensional configuration. While the particular three dimensional configuration may be varied for optimum medical efficiency, the twisted three dimensional configuration typically bears some resemblance to a pretzel.

Figure 2:
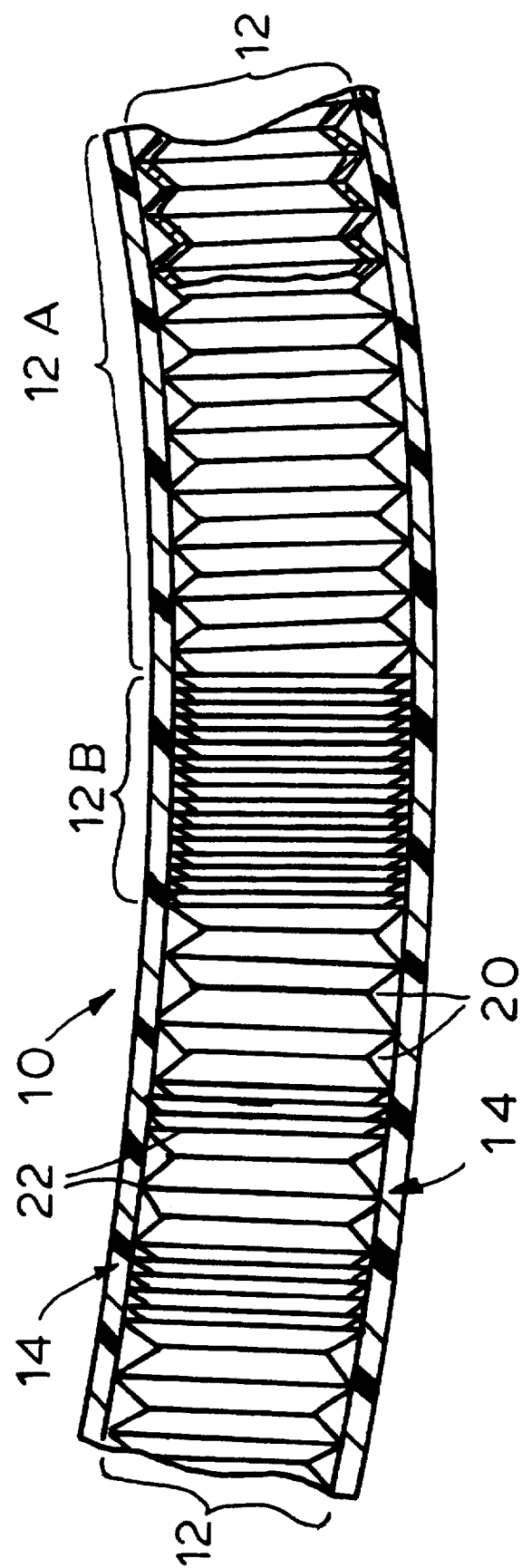
FIG. 2 is a fragmentary sectional view, to an enlarged scale, of the core in expanded and contracted orientations.

Referring now to FIG. 2 in particular, it is a critical feature of the present invention that the longitudinal dimension of the core 12 along its longitudinal axis be modifiable within limits by manual pressure both before and after insertion of the pessary 10 into a vagina. In other words, the longitudinal dimension of the core 12 along its modified longitudinal axis should be modifiable within limits either by the doctor or the patient both before insertion after the pessary 10 has been inserted into the vagina. This is achieved by providing a core 12 which is non-resiliently expandable and contractible within limits to modify the longitudinal dimension of the core 12. A flexible core 12 having a modifiable longitudinal dimension is preferably provided by the use of corrugated tubing defining alternating grooves 20 and ridges 22. The grooves 20 are non-resiliently expandable (as illustrated at 12A) and contractible (as illustrated at 12B) within limits so that the separation between the ridges 22 may be increased or decreased to modify the longitudinal dimension of the core 12. Once the core 12 has been expanded or contracted to modify the longitudinal dimension, typically the longitudinal dimension will, in the absence of any forces applied to the core, retain its modified longitudinal dimension. Of course, when an appropriate force is applied to the core 12, either to expand or contract the same, the grooves 20 will expand or contract to modify the separation between the ridges 22 and thereby modify within limits the longitudinal dimension of the core.

A preferred corrugated tubing according to the present invention is available as non-conductive anesthesia breathing circuit tubing (from Baxter Health Care Corp. of Deerfield, Ill., Dow Corning, or 3M Health Care). The tubing is formed from a plastic such as silicone. A preferred minimum inner diameter is 0.75", and a preferred maximum outer diameter is 1.5". The tubing may be provided to the manufacturer of the pessary in a closed-loop twisted three dimensional configuration ready for covering by the casing 14 or, more likely, as a length of tubing having two ends which must be joined together after the length of tubing is formed into a twisted three dimensional configuration.

Figure 3:
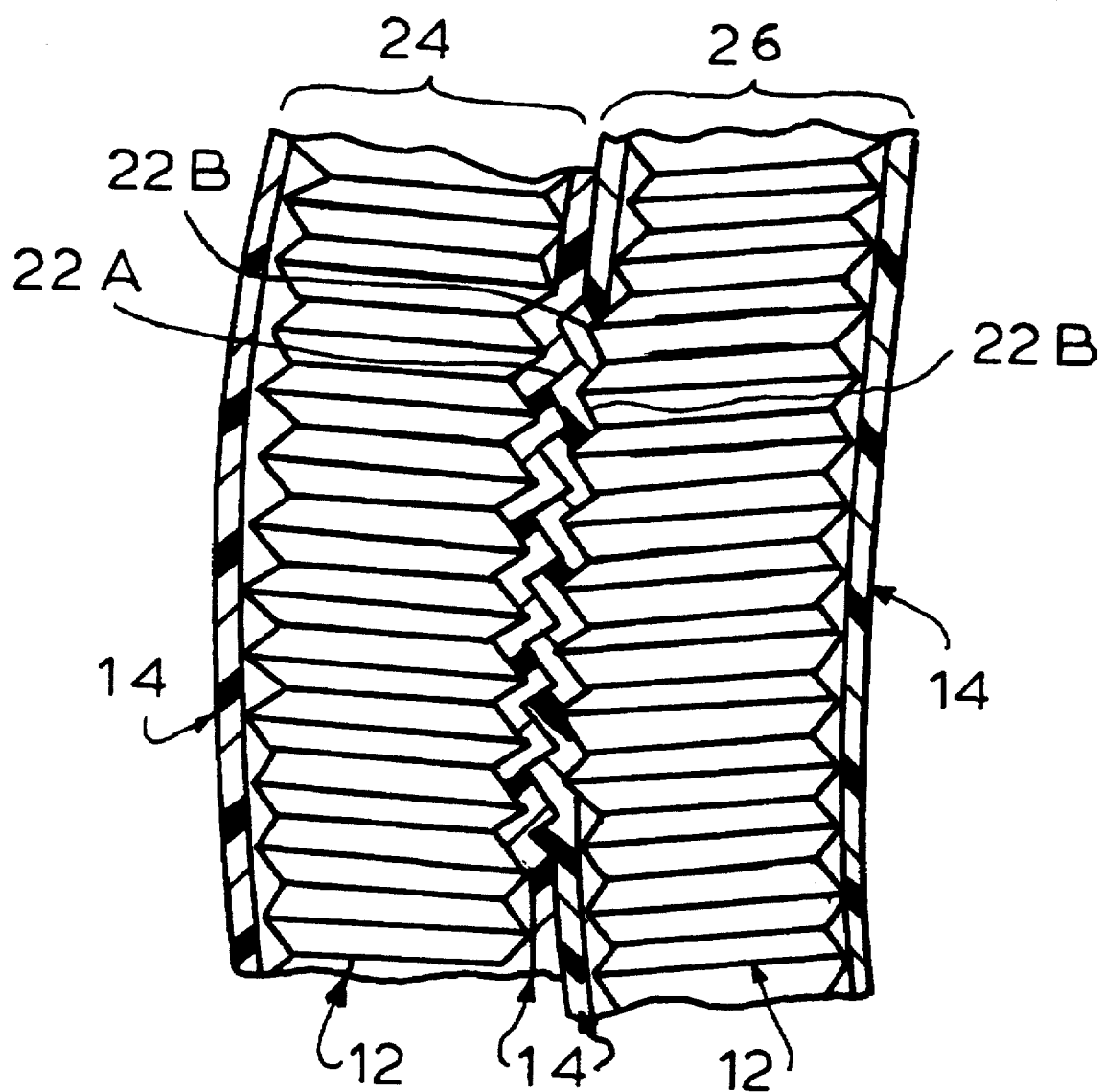
FIG. 3 is a fragmentary sectional view of two longitudinal portions of the pessary meshingly engaging.

Referring now to FIG. 3 in particular, it is another critical feature of the present invention that a first longitudinal portion 24 of the core 12 is manually meshingly engageable with a second longitudinal portion 26 of the core 12, where the first and second longitudinal portions 24, 26 intersect, thereby to lock or fix within limits the longitudinal dimension of the core 12 intermediate the first and second longitudinal portions 24, 26 (i.e., at least one loop 30), both before and after insertion of the pessary 10 into the vagina. Additionally, the first and second longitudinal portions 24, 26 must be manually separable, thereby to unlock or unfix the longitudinal dimension of the core 12 intermediate the first and second longitudinal portions 24, 26.

More particularly, when the core is formed of the corrugated tubing defining alternating grooves 20 and ridges 22, as described above, at least one ridge 22A along a first longitudinal portion 24 of the core 12 is meshingly engageable with an adjacent pair of the ridges 22B along a second longitudinal portion 26 of the core to form a loop 30. The first and second longitudinal portions 24, 26 of the core intersect to lock within limits the longitudinal dimension of the core intermediate the first and second longitudinal portions 24, 26 (i.e., the longitudinal dimension of the loop 30). Further, the ridge 22A and the adjacent pair of ridges 22B must be manually engageable and separable, both before and after insertion of the pessary into the vagina, thereby to enable locking and unlocking of the longitudinal dimension of the core intermediate the first and second longitudinal portions 24, 26 (i.e., the loop 30).

It will be appreciated that the engagement of one ridge 22 of the first longitudinal portion 24 with a single ridge 22 of the second longitudinal portion 26 does not suffice to fix the longitudinal dimension between the first and second longitudinal portions 24, 26 as such engagement can only limit either the contracting or the expansion of the longitudinal dimension. On the other hand, the meshing engagement of at least one ridge 22A of the first longitudinal portion 24 intermediate an adjacent pair of ridges 22B of the second longitudinal portion 26 has the desired effect. Preferably, at least an adjacent pair of the ridges 22A along the first longitudinal portion 24 of the core 12 meshingly engages at least an adjacent pair of the ridges 22B along the second longitudinal portion 26 of the core 12.

The intersection of the first and second longitudinal portions 24, 26 of the core 12 preferably has a parallel component (relative to the longitudinal axis) so that the ridges of one longitudinal portion may fit between ridges of the second longitudinal portion. However, the longitudinal portions need not be strictly parallel and may be almost transverse (that is, at right angles) and still perform the desired locking function of the present invention.

It will be appreciated that the longitudinal dimension of a loop 30 formed by and between two intersecting longitudinal portions 24, 26 of the core 12 may be varied somewhat by manual pressure to expand and contract within limits the longitudinal dimension. However, such limits are well defined, as the maximum and minimum lengths of the loop 30, and this is a much smaller limit range than that which is obtainable only by locking the ends of the core 12 together (the difference in the latter case being the difference between the fully compacted and fully extended lengths of the entire untwisted core 12). Thus, the longitudinal dimension of an average 10 cm core 12 (fully contracted) may expand to 15 cm, while the longitudinal dimension of one of, for example, three 3 cm loops thereof (fully contracted) may expand to 4.5 cm. Clearly, the variability limits for the entire core 12 are substantially higher than those for an individual loop 30 thereof.

A flexible casing 14 of bio-compatible and deformable material encloses the core 12 so as to minimize, and preferably entirely prevent, sore spots and ulcers on the intravaginal walls as a result of the presence of the pessary. While the literature is replete with discussions of the merits (i.e., the advantages and disadvantages) of various flexible casings of bio-compatible and deformable material, it is not within the province of the present application to elect any one such material, or even any one type of material, as being superior. The only limitation imposed on the material used for the casing 14 is that it be capable of enclosing the core 12 without precluding the aforedescribed locking and unlocking thereof. A preferred material for use as the casing of the present invention is a silicone copolymer rubber gel, available under the trade name NUSIL (from Nusil Corp. of Medina, WI or Carpentria, Calif.). The NUSIL gel is formed of a silicone copolymer rubber gel formed on the core by repeated dippings of the core into a liquid formulation of the gel.

To summarize, the present invention provides an intravaginal pessary for treating prolapse wherein the longitudinal length of the pessary intermediate two parts thereof may be fixed within limits. The longitudinal dimension may be locked or fixed within limits or unlocked or unfixed so as to enable modification thereof.

Now that the preferred embodiments of the present invention have been shown and described in detail, various modifications and improvements thereon will become readily apparent to those skilled in the art. Accordingly, the spirit and scope of the present invention is to be construed broadly and limited only by the appended claims, and not by the foregoing specification.

We claim:

1. An intravaginal pessary for treating prolapses comprising:
    A) a flexible core having a longitudinal axis and being disposed in a twisted three dimensional configuration, the longitudinal dimension of said core along its longitudinal axis being modifiable within limits by manual pressure both before and after insertion of said pessary into a vagina, said core being non-resiliently expandable and contractible within limits to modify the longitudinal dimension of said core;
        a first longitudinal portion of said core being meshingly engageable with a second longitudinal portion of said core intersecting said first longitudinal portion of said core to lock within limits the longitudinal dimension of said core intermediate said first and second longitudinal portions, both before and after insertion of said pessary into the vagina;
        said first and second longitudinal portions being manually separable, both before and after insertion of said pessary into the vagina, to unlock the longitudinal dimension of said core intermediate said first and second longitudinal portions; and
    B) a flexible casing of bio-compatible and deformable material enclosing said core without precluding such locking and unlocking thereof.

2. An intravaginal pessary for treating prolapses comprising:
    A) a flexible core having a longitudinal axis and being disposed in a twisted three dimensional configuration, the longitudinal dimension of said core along its longitudinal axis being modifiable within limits by manual pressure both before and after insertion of said pessary into a vagina, said core being formed of corrugated tubing defining alternating grooves and ridges, said grooves being non-resiliently expandable and contractible within limits to modify the longitudinal dimension of said core;
        at least one of said ridges along a first longitudinal portion of said core being meshingly engageable with an adjacent pair of said ridges along a second longitudinal portion of said core intersecting said first longitudinal portion of said core to lock within limits the longitudinal dimension of said core intermediate said first and second longitudinal portions, both before and after insertion of said pessary into the vagina;
        said at least one ridge and said adjacent pair of ridges being manually separable, both before and after insertion of said pessary into the vagina, to unlock the longitudinal dimension of said core intermediate said first and second longitudinal portions; and
    B) a flexible casing of bio-compatible and deformable gel enclosing said core without precluding such locking and unlocking thereof.

3. The pessary of claim 2 wherein only one of said ridges along the first longitudinal portion of said core meshingly engages at least an adjacent pair of said ridges along the second longitudinal portion of said core.

4. The pessary of claim 3 wherein said only one ridge and said adjacent pair of said ridges are manually engageable and separable.

5. The pessary of claim 2 wherein at least an adjacent pair of said ridges along the first longitudinal portion of said core meshingly engage at least an adjacent pair of said ridges along a second longitudinal portion of said core.

6. The pessary of claim 5 wherein said two adjacent pairs of said ridges are manually engageable and separable.

7. The pessary of claim 1 wherein said core is hollow.

8. An intravaginal pessary for treating prolapses comprising:
    A) a flexible hollow core having a longitudinal axis and being disposed in a twisted three dimensional configuration, the longitudinal dimension of the core along its longitudinal axis being modifiable within limits by manual pressure, both before and after insertion of said pessary into a vagina, said core being formed of corrugated tubing defining alternating grooves and ridges, said grooves being non-resiliently expandable and contractible within limits to modify the longitudinal dimension of said core;
        at least one of said ridges along a first longitudinal portion of said core being meshingly engageable with at least an adjacent pair of said ridges along a second longitudinal portion of said core intersecting said first longitudinal portion of said core to lock within limits the longitudinal dimension of said core intermediate said first and second longitudinal portions, both before and after insertion of said pessary into the vagina;

said at least one ridge and said adjacent pair of ridges being manually separable, both before and after insertion of said pessary into the vagina, to unlock the longitudinal dimension of said core intermediate said first and second longitudinal portions; and B) a flexible casing of bio-compatible and deformable gel enclosing said core without precluding such locking and unlocking thereof.

9. A method of treating prolapse of a vagina by use of a pessary, comprising the steps of:

A) providing a pessary formed of
  i) a flexible hollow core having a longitudinal axis and being disposed in a twisted three dimensional configuration, the longitudinal dimension of the core along its longitudinal axis being modifiable within limits by manual pressure both before and after insertion of the pessary into a vagina, the core being formed of corrugated tubing defining alternating grooves and ridges, the grooves being non-resiliently expandable and contractible within limits to modify the longitudinal dimension of the core;
    at least one of the ridges along a first longitudinal portion of the core being meshingly engageable with at least an adjacent pair of the ridges along a second longitudinal portion of the core intersecting the first longitudinal portion of the core to lock within limits the longitudinal dimension of the core intermediate the first and second longitudinal portions, both before and after insertion of the pessary into the vagina;
    the one ridge and the adjacent pair of ridges being manually separable, both before and after insertion of the pessary into the vagina, to unlock the longitudinal dimension of the core intermediate the first and second longitudinal portions; and
  ii) a flexible casing of bio-compatible and deformable material enclosing the core without precluding such locking and unlocking;

B) manually separating the at least one ridge and the adjacent pair of ridges, thereby to unlock the longitudinal dimension;

C) expanding or contracting the grooves to modify the longitudinal dimension; and D) meshingly engaging at least one ridge and one adjacent pair of ridges, thereby to lock the longitudinal dimension.

* * * * *